United States Patent [19]

van Gemen et al.

[11] Patent Number: 5,834,255

[45] Date of Patent: Nov. 10, 1998

[54] QUANTIFICATION OF NUCLEIC ACID

[75] Inventors: Bob van Gemen, TD Boxtel; Tim Kievits, XB Vught; Peter F. Lens, EW Den Bosch, all of Netherlands

[73] Assignee: Akzo Nobel N.V., Arnhem, Netherlands

[21] Appl. No.: 385,392

[22] Filed: Feb. 7, 1995

Related U.S. Application Data

[63] Continuation of Ser. No. 167,456, Dec. 15, 1993, abandoned, which is a continuation of Ser. No. 924,133, Aug. 3, 1992, abandoned.

[30] Foreign Application Priority Data

Aug. 2, 1991 [EP] European Pat. Off. .............. 91202000

[51] Int. Cl.$^6$ .............................. C12P 19/34; C12Q 1/68; C07H 21/04

[52] U.S. Cl. .......................... 435/91.21; 435/6; 435/91.2; 435/91.51; 435/810; 536/24.33; 935/8; 935/77; 935/78

[58] Field of Search .......................... 435/6, 91.2, 91.51, 435/975, 810, 91.21; 536/24.3, 24.33; 935/8, 77, 78

[56] References Cited

U.S. PATENT DOCUMENTS

| | | | |
|---|---|---|---|
| 5,213,961 | 5/1993 | Bunn et al. | 435/6 |
| 5,476,774 | 12/1995 | Wang et al. | 435/91.2 |

FOREIGN PATENT DOCUMENTS

| | | | |
|---|---|---|---|
| WO 90/06995 | 6/1990 | WIPO | C12N 9/12 |
| WOA9102815 | 3/1991 | WIPO | C12Q 1/68 |
| WOA9102817 | 3/1991 | WIPO | C12Q 1/68 |

OTHER PUBLICATIONS

Kwoh et al. Proc. Natl. Acad. Sci. USA 86:1173–1177, Feb. 1989.

Borger et al editors Methods in Enzymology 152:330–335, 1987.

Studencki, Anna, et al., Discrimination among the Human BA, BS, and BC–Globin Genes Using Allele–Specific Oligonucleotide Hybridization Probes, Am. J. Hum. Genet. 37:42–51, 1985.

Cech, Thomas, Ribozymes, Editorial Comments, U.S. Biochemical, vol. 16(2):1–5, 1989.

G. Gilliland et al., *Proc. Natl. Acad. Sci, USA*, 87:2725–2729, Apr. 1990.

1988 Stratagene Catalog, p. 39.

Cech, T.R. et al. Biological catalysis by RNA. Ann. Rev. Biochem (1986) 55:599–629.

Moss, B.A. et al. Sequence of PNA complementary to a small RNA segment of influenza virus A/NT/60/68. Nucl. Acids Res. (1981) 9:1941–1947.

Gen Bank Locus FLADIM a lighment with SEQ 10102 Complement 30–Jun.–1987.

B. Lambe et al., "Quantitation of Epstein–Barr Virus (EBV) Utilizing the Polymerase Chain Reaction (PCR)," Abst An Meet Am Soc Microbiol, vol. 90, p. 114, 1990, USA.

M. Becker–Andre, "Absolute mRNA Quanitification Using the Polymerase Chain Reaction (PCR). A Novel Approach by a PCR aided Transcript Titration Assay (Patty)," Nucleic Acid Reseach, vol. 17, No. 22, pp. 9437–9446, 1989, USA.

R.K. Saiki et al., "Analysis of Enzymatically Amplified Baet–Globin and HLA–DQalpha DNA with Allele–Specific Oligonucleotide Probes," Nature vol. 324, pp. 163–166, 13 Nov. 1986, London, GB.

*Primary Examiner*—W. Gary Jones
*Assistant Examiner*—Debra Shoemaker
*Attorney, Agent, or Firm*—Mary E. Gormley

[57] ABSTRACT

Disclosed is a method of quantifying a target nucleic acid in a test sample by adding to the test sample a known number of molecules of a corresponding nucleic acid comprising a well-defined mutant sequence. Said mutant sequence being discriminatory from the target nucleic acid. Subsequently a competitive amplification reaction of the nucleic acid is performed after which quantification of the amplified nucleic acid is performed by a differential detection.

12 Claims, 4 Drawing Sheets

5,834,255

QUANTIFICATION OF NUCLEIC ACID

This is a continuation of application Ser. No. 08/167,456 filed Dec. 15, 1993, now abandoned which is a continuation of application Ser. No. 07/924,133 filed Aug. 3, 1992, now abandoned.

The invention relates to a method for quantification of target nucleic acid in a test sample. A test kit for carrying out said method is also part of the invention.

BACKGROUND OF THE INVENTION

A method for carrying out the amplification of nucleic acid in a test sample has been disclosed among others by Cetus Corp. in U.S. Pat. Nos. 4,683,195 and 4,683,202 the so-called polymerase chain reaction (PCR).

Recently another method for amplification of nucleic acid in a test sample, especially RNA sequences, has been disclosed in European Patent Application EP 0,329,822 by Cangene Corp. now also U.S. Pat. Nos. 5,409,818 and 5,554,517. The process itself will not be discussed here in detail, but it concerns the so-called NASBA technique (= nucleic acid sequence based amplification).

Amplification is an exponential process. Small differences in any of the variables which control the reaction rate will lead to dramatic differences in the yield of the amplified product. PCR as well as NASBA have wide-spread applications in genetic disease diagnosis however, these techniques only provide qualitative results.

A need exists for a method of quantifying directly, accurately, and in a reproducible manner, the amount of a specific nucleic acid present in a test sample.

A sensitive, reproducible, quantitative analysis of a test sample obtained from a patient suffering from an infectious disease, e.g. AIDS or hepatitis, can be of utmost importance in determining the extent of the infectious agent present in the patient, which information is useful in monitoring the patient treatment.

BRIEF DESCRIPTION OF THE INVENTION

The present invention provides a method of quantifying a target nucleic acid in a test sample comprising adding a known number of molecules of a corresponding nucleic acid comprising a well-defined mutant sequence to the test sample, said mutant sequence being discriminatory from the target nucleic acid, but amplifiable with comparable efficiency, subsequently performing an amplification reaction of the nucleic acid, after which quantification of the amplified nucleic acid is performed by differential detection.

The target nucleic acid can be deoxyribonucleic acid (DNA) as well as ribonucleic acid (RNA).

Preferably the target nucleic acid sequence is ribonucleic acid. The differential detection necessary in this method is performed by using a probe sequence able to hybridize with both the target nucleic acid and the mutant sequence as well, or using two probes discriminating the target sequence and mutant sequence.

Said differentiation can also be performed by using a ribozyme capable of cleaving the mutant sequence, while the target sequence will not be cleaved by the ribozyme used or vice versa.

A part of the invention includes a test kit for carrying out the previously described methods.

DETAILED DESCRIPTION OF THE INVENTION

Figure 1:
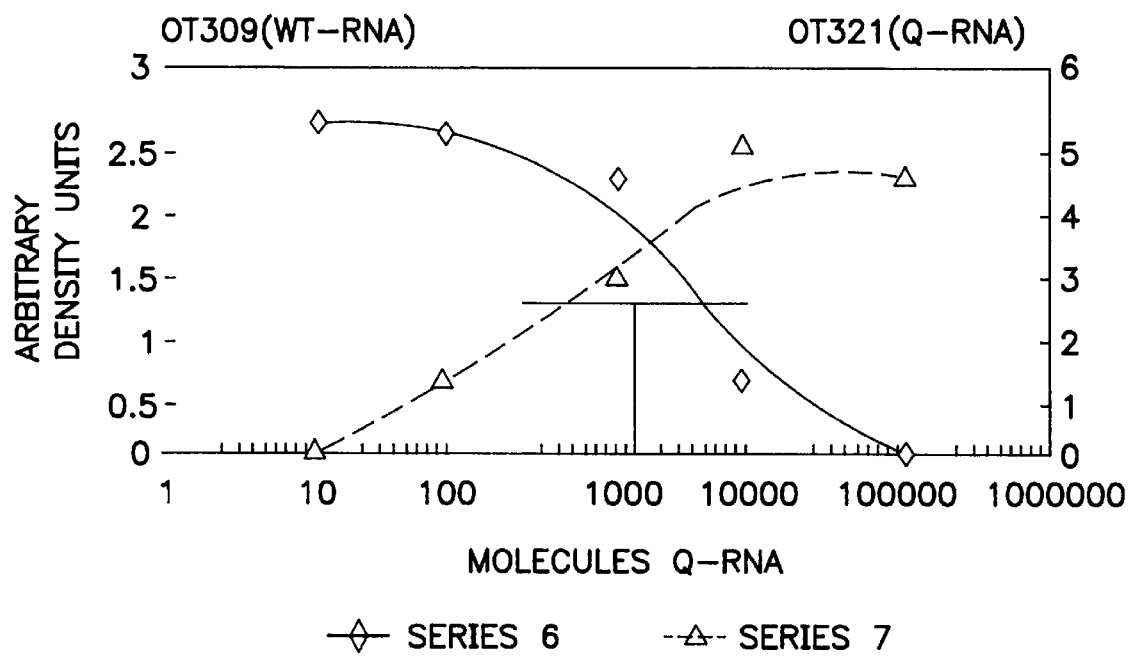
FIGS. 1, 2 and 3 are graphs of the results of competitive NASBA reactions, with a variance of input molecules.

Recently patent application WO 91/02817 was published in which a co-amplification of an internal standard nucleic acid segment and target sequence was described. The method used in this application is not a competition reaction. In contrast to the instant invention quantification in that application is performed by measuring the signals obtained and subsequently determining the ratio between both sequences amplified. The present invention differs significantly from that process since, among other things, competition between wild-type (target nucleic acid) and well-defined mutant sequence is an essential part of the instant invention.

The method according to the instant invention is based on the principle of competitive amplification of nucleic acid from a clinical sample containing an unknown concentration of wild-type target nucleic acid, to which has been added a known amount of a well-defined mutant sequence.

Amplification of both target nucleic acid and mutant sequence as well is preferably performed with one primer set including two primers of which each primer hybridizes to the target nucleic acid and mutant sequence with the same efficiency.

This competitive amplification is performed with a fixed amount of (clinical) sample and dilution series of mutant sequence or vice versa.

The mutation in the added sequence is necessary for discriminatory detection of the wild-type and mutated amplified sequences with wild-type and mutation specific labelled oligonucleotides respectively.

This means that after competitive amplification samples are analysed in duplo using any sequence specific detection, for example:

1. gel electrophoresis, blotting, hybridization, autoradiography, scanning;
2. Slot-blotting, hybridization, autoradiography, scanning.;
3. Non-capture bead based assay, counting; and
4. Capture bead based assay, counting.

The initial ratio of wild-type and mutated sequences will be reflected in the ratio of wild-type and mutated signals. At a 1:1 ratio and equal efficiency of amplification, the reduction in signal for both wild-type and mutated sequence will be 50%. So at the dilution of mutated nucleic acid that causes a 50% reduction in signal the amount of mutated nucleic acid equals the amount of wild-type nucleic acid in the (clinical) sample.

Using a well-defined mutant sequence comprising, for instance, in the sequence a single base mutation (e.g. an A→G transition) just one restriction enzyme, or a ribozyme, has to be used to discriminate between target nucleic acid and the mutant sequence.

Subsequently just one analysis (for instance one gel system) is necessary in order to quantify the target nucleic acid.

Samples suitable for analysis by this method may be of human or non-human origin. The samples may be derived from cultured samples, for instance, mononuclear cells, or isolated from dissected tissue. Also blood and blood plasma, as well as brain-liquor, urine, etc. can be used as test sample material.

If, for example, the test sample is blood with a target virus to be quantified according to the invention, the viral nucleic acid can be extracted from the test sample. In order to obtain a very fast, simple and reproducible procedure according to the invention the well-defined mutant sequence can be added before, during or after the target nucleic acid extraction without interference in the extraction procedure. Subsequently the competitive amplification and differential detection according to the invention can be performed directly after the extraction procedure.

Due to its high sensitivity, speed, reproducibility and accuracy, the present method can be used to quantify exactly the amount of, for instance, viruses like AIDS-VIRUS or hepatitis virus in the test sample obtained from a patient suspected of suffering from the disease.

It can be of prime importance to know at different stages in a disease the exact amount of viruses or other disease-causing agents in order, for example, to know the dose of medication to be administered to the patient.

The test kit according to the invention is provided in its simplest embodiment with a well-defined mutant sequence and appropriate oligonucleotides viz. primers/primer pair in order to perform the desired amplification reaction and a probe sequence or ribozyme as well.

Additionally, a test kit can be supplied with the appropiate enzymes in order to carry out the amplification reaction.

The method according to the invention is illustrated by the following examples.

EXAMPLE I

In vitro generated wild-type (WT) and mutant (Q) RNA were used to prove the principle of quantitative NASBA. Plasmids used for in vitro RNA synthesis contained a 1416 bp fragment of the HIV-1 sequence resulting from a partial Fok 1 restriction enzyme digest (nucleotides 1186–2638 of the HIV-1hxb2 sequence, Ratner et al., 1987) cloned in pGEM3 or pGEM4 (Promega). The sequence between the restriction sites PstI (position 1418 on HIV-1 hxb2) and Sph I (position 1446 on HIV-1 hxb2) was changed from GAATGGGATAGAGTGCATCCAGTGCATG (OT309) (SEQ ID NO:1) in the WT to GACAGTGTAGATAGAT-GACAGTCGCATG (OT321) (SEQ ID NO:2) in the Q RNA. In vitro RNA was generated from these constructs with either T7 RNA polymerase or SP6 RNA polymerase. (Sambrook et al., 1989).

Reaction mixtures were treated with DNase to remove plasmid DNA. After phenol extraction and ethanol precipitation the recovered RNA was quantitated on ethidium bromide stained agarose gels by comparison to a calibration series of known amounts of ribosomal RNA. The RNA solutions were diluted to the desired concentrations and used as input for amplification by NASBA as described in EP 0329,822 (now also U.S. Pat. Nos. 5,409,818 and 5,554, 517). Primers used for amplification were OT 270: (AATTCTAATACGACTCACTATAGGGGTGCTATGTC-ACTTCCCCTTGGTTCTCTCA (SEQ ID NO:3), P1) and OT271 (AGTGGGGGGACATCAAGCAGCCATGCAAA, (SEQ ID NO:4) P2), generating a RNA molecule complementary to the HIV-1hxb2 sequence of 142 nt (pos 1357 to 1499). Detection of 10 μl of each amplification has been performed by electrophoresis in duplo on 3% NuSieve, 1% agarose gels (Sambrook et al., 1989) blotted onto Zeta-Probe (Biorad) using a vacuumblot apparatus (Pharmacia) and hybridized with $^{32}p$ labelled oligonucleotides specific for either the WT or the Q RNA sequence between above mentioned Sph1 and Pst 1 sites. Exposure times to X-ray films (Kodak) ranged from 30 minutes to 3 days.

Films were scanned with a LKB Ultroscan XL densitometer for quantification of the signal in the bands. Number of target molecules of both WT and Q RNA are listed in table 1.

TABLE 1

| Tube | Copies W.T. RNA | Copies Q RNA |
|------|-----------------|--------------|
| 1 | $10^3$ | $10^1$ |
| 2 | $10^3$ | $10^2$ |
| 3 | $10^3$ | $10^3$ |
| 4 | $10^3$ | $10^4$ |
| 5 | $10^3$ | $10^5$ |

As control amplification of WT RNA or Q RNA alone was performed. The results of the competitive NASBA are presented in FIG. 1. At the mean of the 50% reduction for both WT and Q RNA the number of input molecules is approximately $10^3$ molecules Q RNA, which equals the number of WT RNA molecules.

The formula used for determining the mean of 50% reduction for both Q and WT RNA is as follows:

$$\log (conc.\ W.T.) = \frac{\log ([Q] 50\%\ Sig\ Q) + \log ([Q] 50\%\ Sig.\ WT)}{2}$$

in which ([Q] 50% Sig. Q) is the number of Q RNA molecules at which the signal using OT 321, specific for Q RNA, is only 50% of the signal obtained when Q RNA alone is amplified and ([Q] 50% Sig. WT) is the number of Q RNA molecules at which the signal using OT 309, specific for WT RNA, is only 50% of the signal obtained when WT RNA alone is amplified.

EXAMPLE II

This experiment was performed the same way as was example 1, except that the input RNA molecules are those given in Table 2 below

TABLE 2

| Tube | copies W.T. RNA | copies Q RNA |
|------|-----------------|--------------|
| 1 | $10^4$ | $10^2$ |
| 2 | $10^4$ | $10^3$ |
| 3 | $10^4$ | $10^4$ |
| 4 | $10^4$ | $10^5$ |
| 5 | $10^4$ | $10^6$ |

Figure 2:
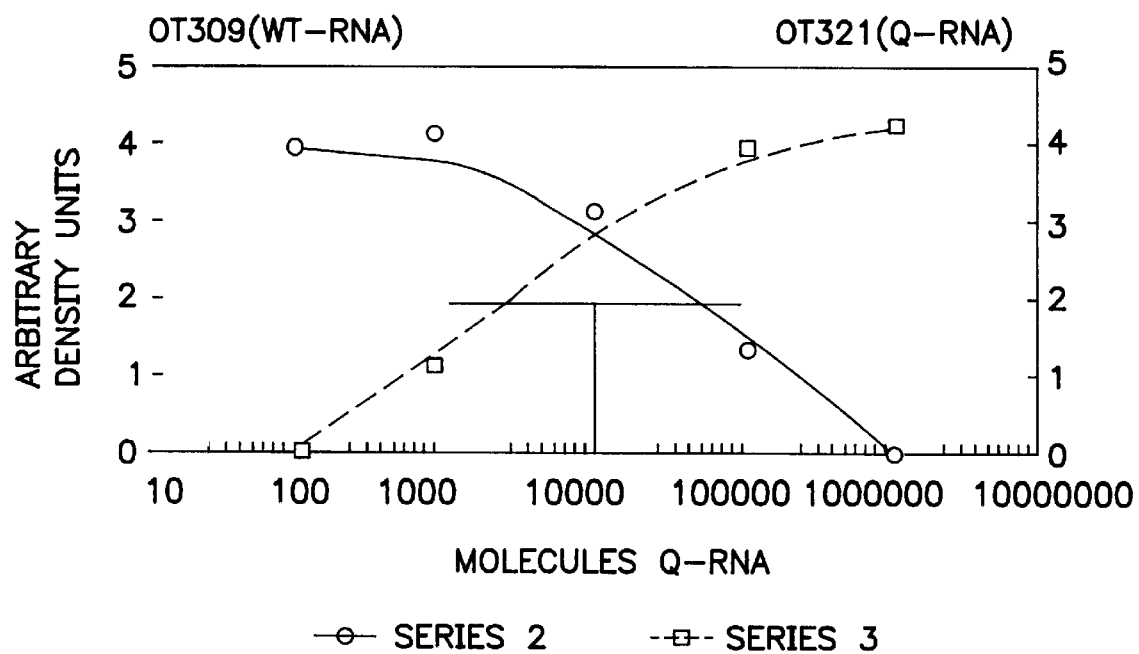

The results presented in FIG. 2 show an input of $10^4$ molecules of WT RNA using the formula.

$$\log \cdot (conc.\ WT) = \frac{\log ([Q] Sig\ Q\ 50\%) + \log ([Q] Sig.\ WT\ 50\%)}{2}$$

EXAMPLE III

This experiment was performed the same way as was example 1, except that the input RNA molecules are those given in Table 3 below.

TABLE 3

| Tube | copies W.T. RNA | copies Q RNA |
|------|-----------------|--------------|
| 1 | $10^5$ | $10^3$ |
| 2 | $10^5$ | $10^4$ |
| 3 | $10^5$ | $10^5$ |
| 4 | $10^5$ | $10^6$ |
| 5 | $10^5$ | $10^7$ |

Figure 3:
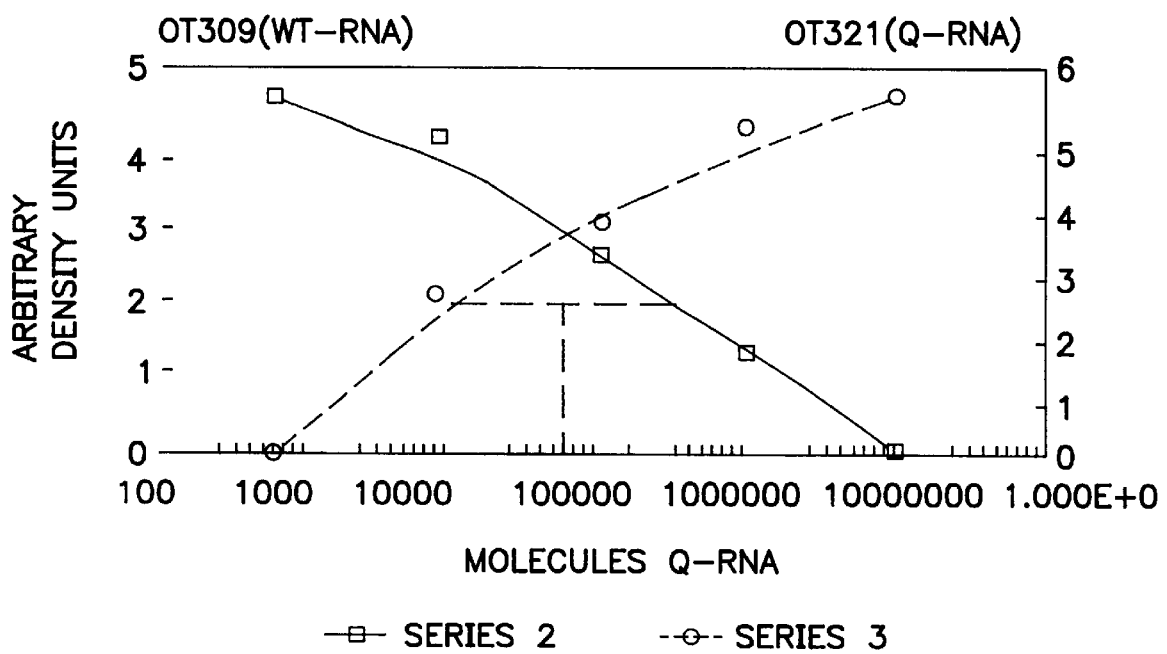

The results presented in FIG. 3 show an input of $6.5 \times 10^4$ molecules of WT RNA using the formula.

$$\log (conc. \; W.T.) = \frac{\log ([Q] \, Sig \, Q \, 50\%) + \log ([Q] \, Sig. \, WT \, 50\%)}{2}$$

EAMPLE IV

Here quantitative NASBA is applied to nucleic acid isolated from plasma of HIV-1 infected individuals. 1 ml plasma samples of 3 sero-positive HIV-1 infected individuals were used to isolate nucleic acid (Boom et al., 1990).

Nucleic acid was finally recovered in 100 μl water. Amplifications were as in example 1 except input RNA molecules were as in table 4.

TABLE 4

| tube | volume nucleic acid sol. | copies Q RNA |
|------|--------------------------|--------------|
| 1 | 2 μl patient 1 | $10^1$ |
| 2 | 2 μl patient 1 | $10^2$ |
| 3 | 2 μl patient 1 | $10^3$ |
| 4 | 2 μl patient 1 | $10^4$ |
| 5 | 2 μl patient 1 | $10^5$ |
| 6 | 2 μl patient 2 | $10^1$ |
| 7 | 2 μl patient 2 | $10^2$ |
| 8 | 2 μl patient 2 | $10^3$ |
| 9 | 2 μl patient 2 | $10^4$ |
| 10 | 2 μl patient 2 | $10^5$ |
| 11 | 2 μl patient 3 | $10^1$ |
| 12 | 2 μl patient 3 | $10^2$ |
| 13 | 2 μl patient 3 | $10^3$ |
| 14 | 2 μl patient 3 | $10^4$ |
| 15 | 2 μl patient 3 | $10^5$ |

Figure 4:
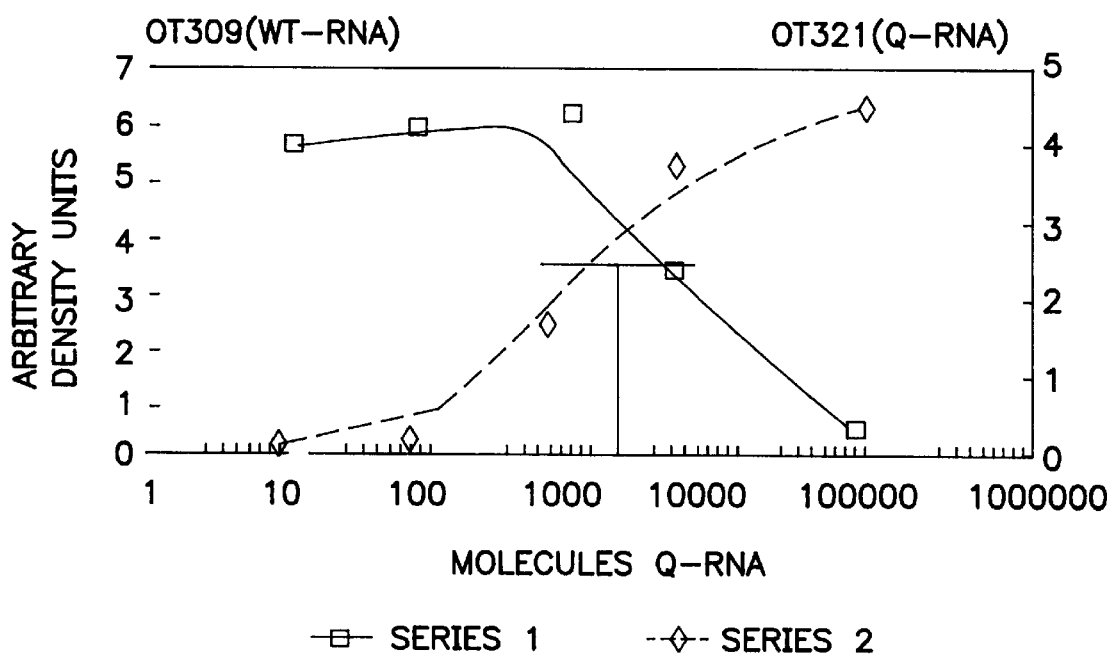
FIGS. 4, 5 and 6 give the results of quantitative NASBA when applied to three sero-positive HIV-1 patient samples.
Figure 5:
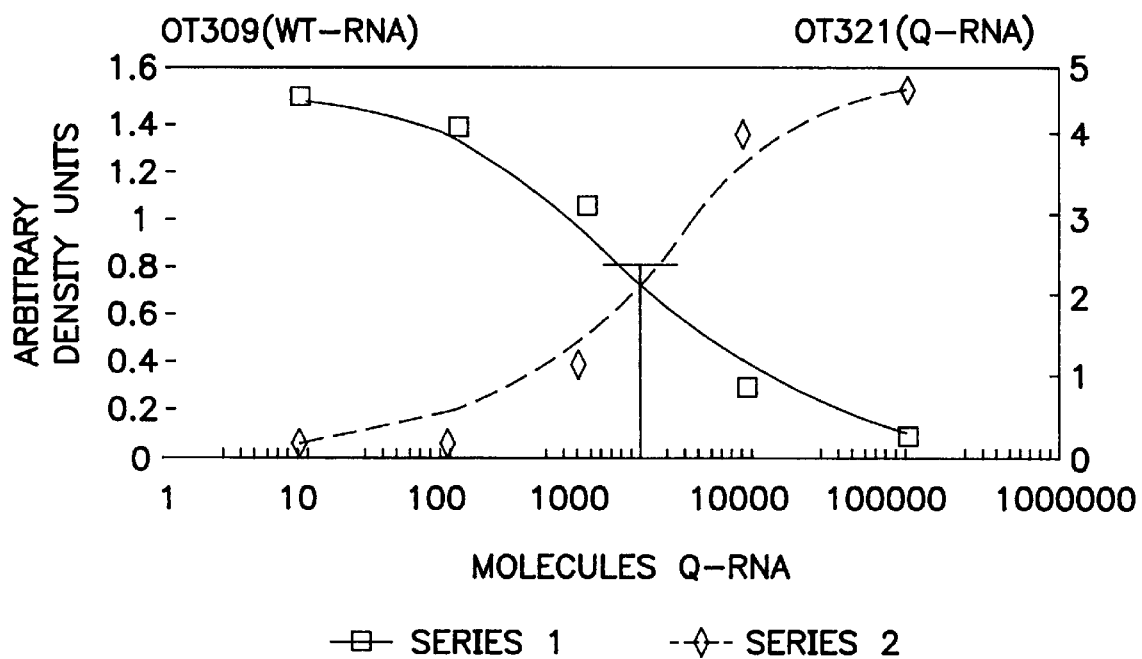
Figure 6:
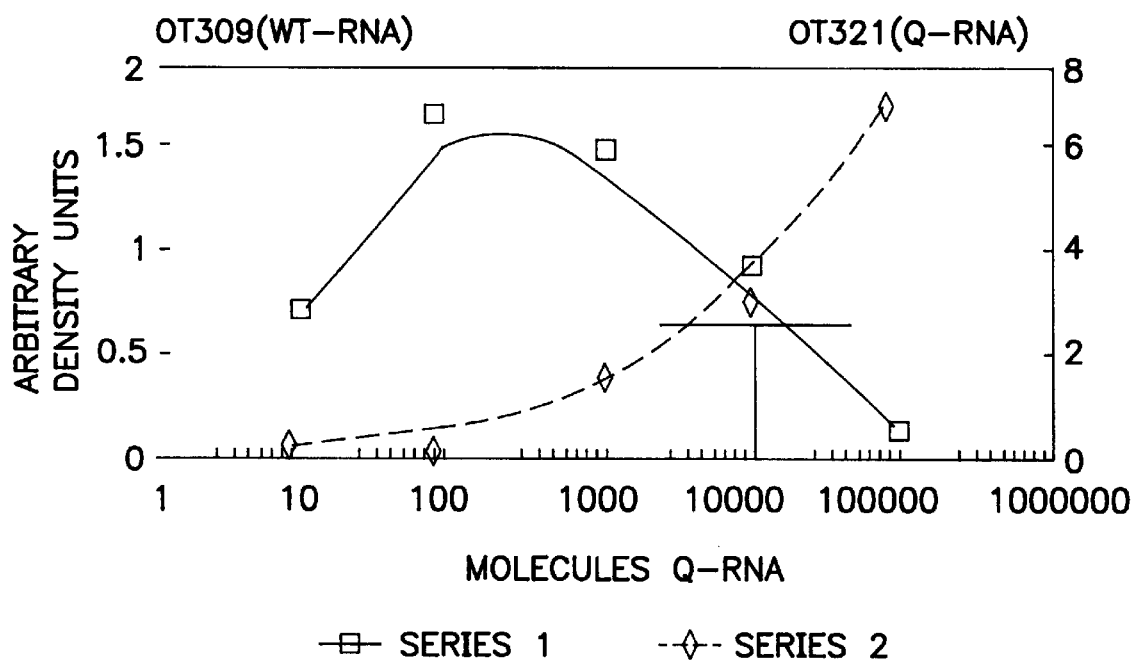

Results are presented in FIGS. 4, 5 and 6 for patients 1, 2 and 3, respectively.

Results indicate the number of W.T. RNA molecules patients 1, 2 and 3 to be $4.5 \times 10^3$, $2.1 \times 10^3$ and $1.2 \times 10^4$ in 2 μl nucleic acid solution, respectively, using the formula:

$$\log (conc. \; WT) = \frac{\log ([Q] \, Sig \, Q \, 50\%) + \log ([Q] \, Sig. \, WT \, 50\%)}{2}$$

EXAMPLE V

This experiment was performed the same way as was example 1 except that the input RNA molecules are as shown in table 5 and that detection of NASBA amplified WT⁻ and Q-RNA is according to the hereafter described method.

Amplified WT⁻ and Q-RNA of 5 μl NASBA reaction was captured on streptavadin coated magnetic dynabeads (Dynal) with the biotinylated oligonucleotide OT 700 (5' Biotin-TGTTAAAAGAGACCHTCAATGAGGA 3') (SEQ ID NO:5) as intermediair. The capture hybridization process takes place at 45° C. for 30 minutes in 100 μl hybridization buffer II (5×SSPE, 0.1% SDS, 0.1% milkpowder, 10 μg/ml denatured salm-sperm DNA; Sambrook et al., 1989). After this step the beads are washed in 2×SSC, 0.1% BSA using a magnet to retain the beads in the reaction tube or microtiter plate.

Subsequently the RNA was hybridized with Horse Radish Peroxidase (HRP) labelled oligonucleotides specific for the WT⁻ or Q-RNA sequence between before mentioned PstI and SphI sites, in 100 μl hybridization buffer II for 30 minutes at 45° C.

Non-hybridized HRP-oligonucleotides are washed away using the same procedure described above. Detection of HRP retained on the beads is accomplished by addition of 100 μl substrate solution (0.45 mM TMB.HCl.H$_2$O, 0.5 mM CTAB, 7.65 g/l Emdex, 27 mM NaCitrate.2H$_2$O, 22.1 mM citric acid.H$_2$O, 2.25 mM urea-peroxid and 5.35 mM 2-chloro-acetamid).

The reaction is stopped at an appropriate time point with 50 μl 250 mM oxalic acid. The amount of substrate conversion from colorless to yellow is determined by measuring the absorbance at 450 nm in an Organon Teknika 510 microplate reader. The $A_{450}$ values for both WT⁻ and Q-probe are analysed as before (FIG. 7).

Figure 7:
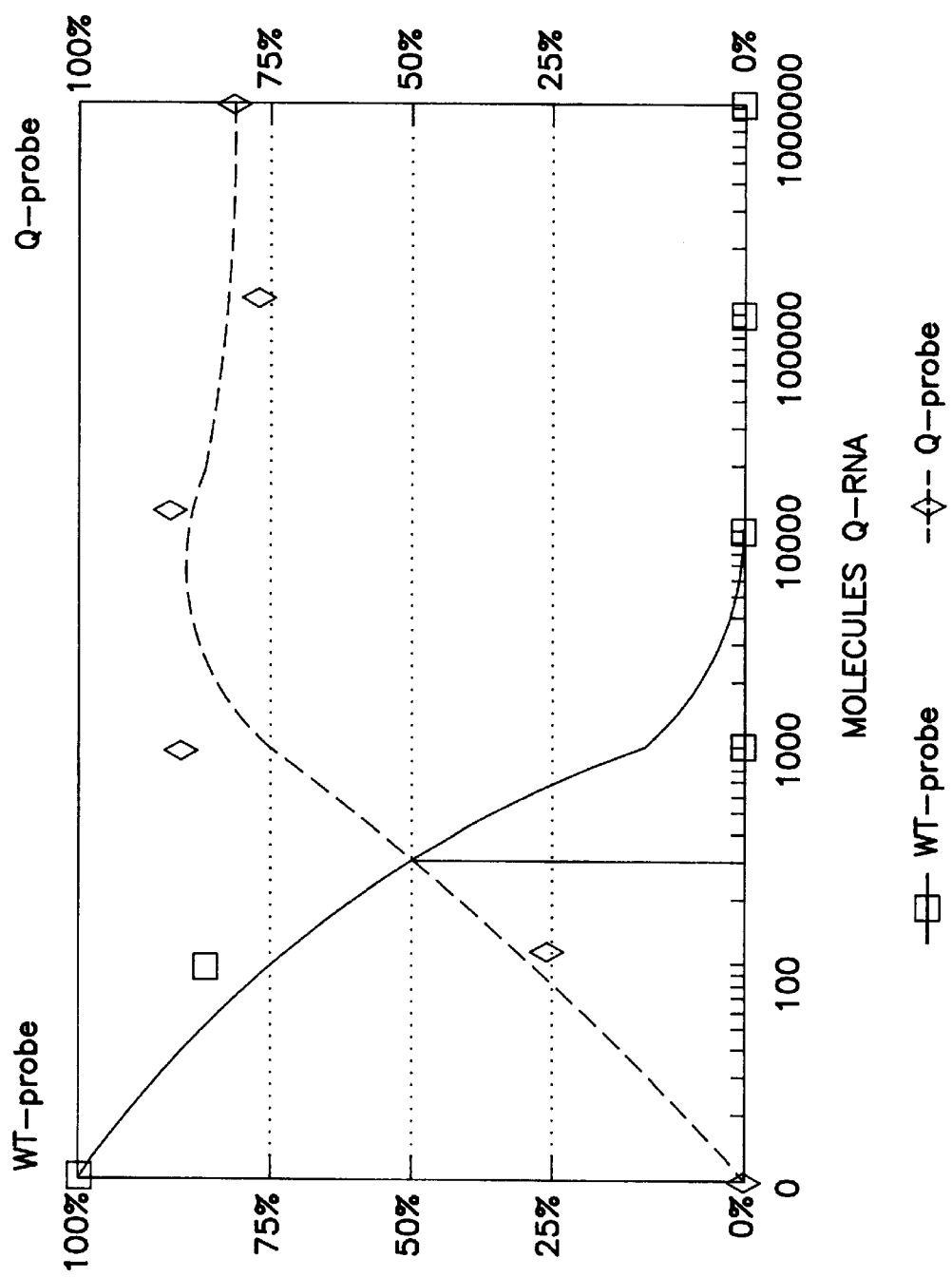
FIG. 7 is a graph of the results of a competitive NASBA reaction.

The results in FIG. 7 show an input of $2.7 \times 10^2$ molecules WT-RNA using the formula:

$$\log (conc. \; WT) = \frac{\log ([Q] \, Sig \, Q \, 50\%) + \log ([Q] \, Sig. \, WT \, 50\%)}{2}$$

TABLE 5

| Tube | copies WT⁻ RNA | copies Q-RNA |
|------|----------------|--------------|
| 1 | $10^2$ | — |
| 2 | $10^2$ | $10^2$ |
| 3 | $10^2$ | $10^3$ |
| 4 | $10^2$ | $10^4$ |
| 5 | $10^2$ | $10^5$ |
| 6 | $10^2$ | $10^6$ |

References

Boom R, Sol C F A, Salimans M M M, Jansen C L, Werthiem - van Dillen PME and Van der Noordaa J. Rapid and simple method for purification of nucleic acids. J. Clin. Microbiol. 1990; 28 : 495–503.

Ratner L, Fisher A, Jagodzinske H H, Mitsuya H., Lion R S, Gallo R C and Wong-Staal F. Complete nucleotide sequence of functional clones of the AIDS virus. AIDS Res. Hum. Retroviruses 1987; 3 : 57–69.

Sambrook J, Maniatis T, Fritsch E. Molecular cloning. A laboratory manual, 2nd edition. Cold Spring Harbor laboratories, Cold Spring Habor, N.Y., 1989.

We claim:

1. A method for quantifying a target nucleic acid in a test sample containing an unknown amount of said target nucleic acid, comprising:

a) adding to the test sample a known quantity of nucleic acid molecules that have the same amplification primer binding sites as the target nucleic acid and are amplifiable with an efficiency comparable to that of the target nucleic acid, but contain a mutation that renders said molecules separately identifiable from the target nucleotide nucleic acid;

b) performing an isothermal transcription-based amplification reaction of the sample from step a) using amplification primers that bind to both the target and mutated nucleic acids; and c) detecting both amplified nucleic acids of step b) using a system that will differentially detect the target and the mutated nucleic acids and generate detection signals; and d) determining the quantity of target nucleic acid in the test sample by comparing the signals obtained for the target nucleic acid to the signals obtained for the known quantity of mutated nucleic acid.

2. The method according to claim 1, wherein the isothermal transcription-based amplification reaction is NASBA.

3. The method according to claim 1, wherein the target nucleic acid and the mutated nucleic acid are RNA.

4. The method according to claim 1, wherein the differential detection is performed by using two nucleic acid probes, one that specifically hybridizes with the target nucleic acid and one that specifically hybridizes with the mutant nucleotide.

5. The method of claim 1, wherein the target nucleic acid and the mutated nucleic acid are composed of substantially the same nucleotides.

6. The method according to claim 5, wherein the mutated nucleic acid contains a single base mutation that creates a site that allows the molecules to be cleaved by a ribozyme, and the differential detection is performed by using a ribozyme that cleaves specifically the mutant nucleotide and not the target nucleic acid.

7. The method of claim 1, wherein the known quantity of mutated nucleic acid is added to the test sample prior to extraction of nucleic acid from the test sample.

8. The method of claim 1, wherein the test sample is of human origin and the target nucleic acid is of viral origin.

9. The method of claim 8, wherein the virus is a human immunodeficiency virus.

10. A test kit for quantifying a target nucleic acid in a test sample containing an unknown amount of said target nucleic acid, comprising:

(a) a defined quantity of nucleic acid molecules that have the same amplification primer binding sites as the target nucleic acid and are ampliflable with an efficiency comparable to that of the target nucleic acid, but contain a mutation that renders said molecules separately identifiable from the target nucleotide nucleic acid;

(b) amplification primers that bind to both the target and mutated nucleic acids; and (c) enzymes for performing an isothermal transcription-based amplification reaction where the enzymes are an enzyme having DNA-dependent DNA polymerase activity, an enzyme having RNA-dependent DNA polymerase activity, an enzyme having ribonuclease H activity and an enzyme having DNA-dependent RNA polymerase activity.

11. The test kit of claim 10, wherein the mutated nucleic acid is RNA.

12. The test kit of claim 11, wherein the enzymes are reverse transcriptase, T7 RNA polymerase, and RNase H.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
GAATGGGATA GAGTGCATCC AGTGCATG                              28
```

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

```
GACAGTGTAG ATAGATGACA GTCGCATG                              28
```

( 2 ) INFORMATION FOR SEQ ID NO:3:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

```
AATTCTAATA CGACTCACTA TAGGGGTGCT ATGTCACTTC CCCTTGGTTC TCTCA    55
```

( 2 ) INFORMATION FOR SEQ ID NO:4:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

```
AGTGGGGGGA CATCAAGCAG CCATGCAAA                             29
```

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

```
TGTTAAAAGA GACCATCAAT GAGGA                                 25
```